(12) United States Patent
Winkler et al.

(10) Patent No.: US 6,749,555 B1
(45) Date of Patent: Jun. 15, 2004

(54) SYSTEM AND METHOD FOR THE TREATMENT OF SPINAL METASTASES

(75) Inventors: Rance A. Winkler, Atlanta, GA (US); Timothy J. Patrick, Alpharetta, GA (US); Carribeth B. Ramey, Suwanee, GA (US)

(73) Assignee: Proxima Therapeutics, Inc., Alpharetta, GA (US)

( * ) Notice: Subject to any disclaimer, the term of this patent is extended or adjusted under 35 U.S.C. 154(b) by 0 days.

(21) Appl. No.: 10/365,977

(22) Filed: Feb. 13, 2003

(51) Int. Cl.$^7$ .................................................. A61N 5/00
(52) U.S. Cl. .......................................................... 600/3
(58) Field of Search ..................... 600/1–7, 8; 606/198, 606/191–194; 604/101.05, 171, 264, 280, 93

(56) References Cited

U.S. PATENT DOCUMENTS

| | | |
|---|---|---|
| 3,324,847 A | 6/1967 | Zoumboulis |
| 3,872,856 A | 3/1975 | Clayton |
| 4,417,576 A | 11/1983 | Baran |
| 4,706,652 A | 11/1987 | Horowitz |
| 4,754,745 A | 7/1988 | Horowitz |
| 4,763,642 A | 8/1988 | Horowitz |
| 4,821,725 A | 4/1989 | Azam et al. |
| 4,867,741 A | 9/1989 | Portnoy |
| 5,015,247 A | 5/1991 | Michelson |
| 5,084,001 A | 1/1992 | Van't Hooft et al. |
| 5,084,015 A | 1/1992 | Moriuchi |
| 5,106,360 A | 4/1992 | Ishiwara et al. |
| 5,112,303 A | 5/1992 | Pudenz et al. |
| 5,152,747 A | 10/1992 | Olivier |
| 5,236,410 A | 8/1993 | Granov et al. |
| 5,422,926 A | 6/1995 | Smith et al. |
| 5,484,384 A | 1/1996 | Fearnot |
| 5,562,594 A | 10/1996 | Weeks |

(List continued on next page.)

FOREIGN PATENT DOCUMENTS

| | | |
|---|---|---|
| EP | 0 340 881 | 10/1992 |
| EP | 0 867 200 | 9/1998 |
| WO | WO 92/10932 | 7/1992 |

(List continued on next page.)

OTHER PUBLICATIONS

Ravinder, Nath, Ph.D. et al., Development of an $^{241}$Am Applicator For Intracavitary Irradiation of Gynecologic Cancers, *I.J. Radiation Oncology, Biology, Physics*, May 1988, vol. 14, pp. 969–978.

Ashpole, R.D. et al., "A New Technique of Brachytherapy for Malignant Gliomas with Caesium–137: A New Method Utilizing a Remote Afterloading System," *Clinical Oncology*, vol. 2, 333–7 (1990).

*Primary Examiner*—Eric F. Winakur
*Assistant Examiner*—Nikita R Veniaminov
(74) *Attorney, Agent, or Firm*—Nutter McClennen & Fish LLP

(57) ABSTRACT

A brachytherapy system for treating metastases on and around a patient's spinous process is provided. The device generally includes a catheter member having a proximal portion, a distal portion, and at least one lumen extending therethrough. The distal portion of the catheter member includes first and second branch members that are adapted to be positioned on opposed sides of a patient's spinous process. The device further includes first and second elongate anchoring elements disposed on the first and second branch members, and optionally can include at least one centering mechanism disposed within each of the first and second anchoring elements. The first and second anchoring elements are preferably adapted to be positioned between a spinous process and transverse process of at least one vertebral body, and to extend along a length of a patient's spinal column, such that the first and second anchoring elements, when expanded, engage and anchor the first and second branch members between the spinous process and transverse process of at least one vertebral body.

43 Claims, 4 Drawing Sheets

U.S. PATENT DOCUMENTS

| | | | |
|---|---|---|---|
| 5,566,221 A | 10/1996 | Smith et al. | |
| 5,720,717 A | 2/1998 | D'Andrea | |
| 5,724,400 A | 3/1998 | Swerdloff et al. | |
| 5,741,253 A | 4/1998 | Michaelson | |
| 5,800,333 A | 9/1998 | Liprie | |
| 5,803,895 A | 9/1998 | Kronholz et al. | |
| 5,851,182 A | 12/1998 | Sahadevan | |
| 5,863,284 A | 1/1999 | Klein | |
| 6,036,631 A | 3/2000 | McGrath et al. | |
| 6,234,952 B1 * | 5/2001 | Liprie | 600/3 |
| 6,267,775 B1 * | 7/2001 | Clerc et al. | 606/198 |
| 6,413,204 B1 | 7/2002 | Winkler et al. | |
| 6,416,457 B1 * | 7/2002 | Urick et al. | 600/3 |
| 6,482,142 B1 * | 11/2002 | Winkler et al. | 600/3 |
| 6,616,629 B1 * | 9/2003 | Verin et al. | 604/101.05 |

FOREIGN PATENT DOCUMENTS

| | | |
|---|---|---|
| WO | WO 99/11325 | 3/1999 |
| WO | WO 99/33515 | 7/1999 |
| WO | WO 99/42163 | 9/1999 |
| WO | WO 93/09724 | 5/1993 |
| WO | WO 97/19723 | 6/1997 |

* cited by examiner

Posterior (Rear) View

SYSTEM AND METHOD FOR THE TREATMENT OF SPINAL METASTASES

FIELD OF THE INVENTION

The present invention relates generally to apparatus for use in treating proliferative tissue disorders, and more particularly to an apparatus for the treatment of such disorders in the body by the application of radiation.

BACKGROUND OF THE INVENTION

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it. Radiation therapy, or surgical excision followed by radiation therapy, is commonly used to treat spinal metastases. Metastases are tumors that have grown in a location that is remote from the site that the tumor started, and spinal metastases result from the spread of cancer cells into a patient's vertebral column.

Radiation therapy can be administered through one of several methods, or a combination of methods, including external-beam radiation, stereotactic radiosurgery, and permanent or temporary interstitial brachytherapy. The term "brachytherapy," as used herein, refers to radiation therapy delivered by a spatially confined radioactive material inserted into the body at or near a tumor or other proliferative tissue disease site. Owing to the proximity of the radiation source, brachytherapy offers the advantage of delivering a more localized dose to the target tissue region.

For example, brachytherapy is performed by implanting radiation sources directly into the tissue to be treated. Brachytherapy is most appropriate where 1) malignant tumor regrowth occurs locally, within 2 or 3 cm of the original boundary of the primary tumor site; 2) radiation therapy is a proven treatment for controlling the growth of the malignant tumor; and 3) there is a radiation dose-response relationship for the malignant tumor, but the dose that can be given safely with conventional external beam radiotherapy is limited by the tolerance of normal tissue. In brachytherapy, radiation doses are highest in close proximity to the radiotherapeutic source, providing a high tumor dose while sparing surrounding normal tissue. Interstitial brachytherapy is useful for treating malignant brain and breast tumors, among others.

While devices exist for delivering radiation to treat metastases, there is still a need for instruments which can be used to provide brachytherapy to target tissue within specific areas of a human body, such as within a patient's spine. In particular, a number of cancers, including spinal cancers as well as other thoracic cancers, can proliferate into a patient's spine. At present, there are no devices configured for treatment of such proliferation, especially where the proliferation extends through more than one vertebra within the spine.

SUMMARY OF THE INVENTION

The present invention generally provides a brachytherapy system for treating metastases on and around a patient's spinous process. In one embodiment, a brachytherapy device is provided having a catheter member including a proximal portion, a distal portion, and at least one lumen extending therethrough. The distal portion of the catheter member includes first and second branch members that are adapted to be positioned on opposed sides of at least one of a patient's spinous process. The device further includes first and second elongate anchoring elements disposed on the first and second branch members. The device is adapted to receive a radiation source through the at least one lumen in the catheter to the first and second branch members for delivering radiation to tissue surrounding the at least one spinous process. The device can also optionally include at least one centering mechanism disposed on each of the first and second branch members. Each centering mechanism is effective to maintain symmetry of the first and second branch members with respect to a patient's spinal column, and/or to receive a radiation source and to deliver the source to a treatment site.

The first and second anchoring elements are preferably adapted to be positioned between a spinous process and transverse process of at least one vertebral body, and to extend along a length of a patient's spinal column, such that the first and second anchoring elements, when expanded, engage and anchor the first and second branch members between the spinous process and transverse process of at least one vertebral body. In an exemplary embodiment, the first and second elongate anchoring elements each have a length adapted to span a plurality of vertebrae.

In another embodiment, the first and second anchoring elements can be first and second outer expandable balloons, and each centering mechanism can be an inner expandable balloon. Each inner expandable balloon preferably has a size adapted to receive a predetermined amount of a fluid radiation source such that varying doses of radiation can be delivered along a length of the outer expandable balloon. More preferably, each inner expandable balloon is effective to position a radiation source at a predetermined distance apart from the first and second outer expandable balloon to provide a minimum absorbed dose for delivering radiation to tissue adjacent to the outer expandable balloons.

In yet another embodiment, a brachytherapy device is provided including an elongate catheter member having a proximal portion, a distal portion, an inflation lumen, and at least one source lumen. A plurality of inner centering mechanisms are disposed around the catheter member and are in communication with a source lumen. In use, the device is adapted to receive a radiation source to deliver radiation to tissue surrounding the device. The device can also optionally include an outer anchoring member disposed around the distal portion of the catheter member and in communication with the inflation lumen. The outer anchoring member is adapted to anchor the catheter member between a spinous process and transverse process of at least one vertebral body, and to extend along a length of a patient's spinal column. The plurality of centering mechanisms are preferably disposed within the outer anchoring member and are effective to maintain symmetry along a length of the distal portion of the elongate catheter member.

In yet another embodiment of the present invention, a method for treating spinal metastases is provided. The method includes the step of providing at least one brachytherapy apparatus for delivering radioactive emissions. The apparatus has a catheter member having proximal and distal ends and at least one lumen extending therethrough, at least one anchoring element disposed proximate to the distal end of the catheter, and a radiation source disposable through the at least one lumen in the catheter for delivering radiation to the tissue surrounding the anchoring element. The method further includes the steps of intraoperatively placing at least one brachytherapy apparatus between a spinous process and transverse process of at least one vertebral body along a length of the patient's spinal column, providing a controlled dose of radiation to tissue surrounding the apparatus, and removing the brachytherapy apparatus. The radiation source is preferably placed into the brachytherapy apparatus after placement of the apparatus between the spinous process and transverse process of at least one vertebral body, and is removed from the apparatus before removal of the apparatus.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
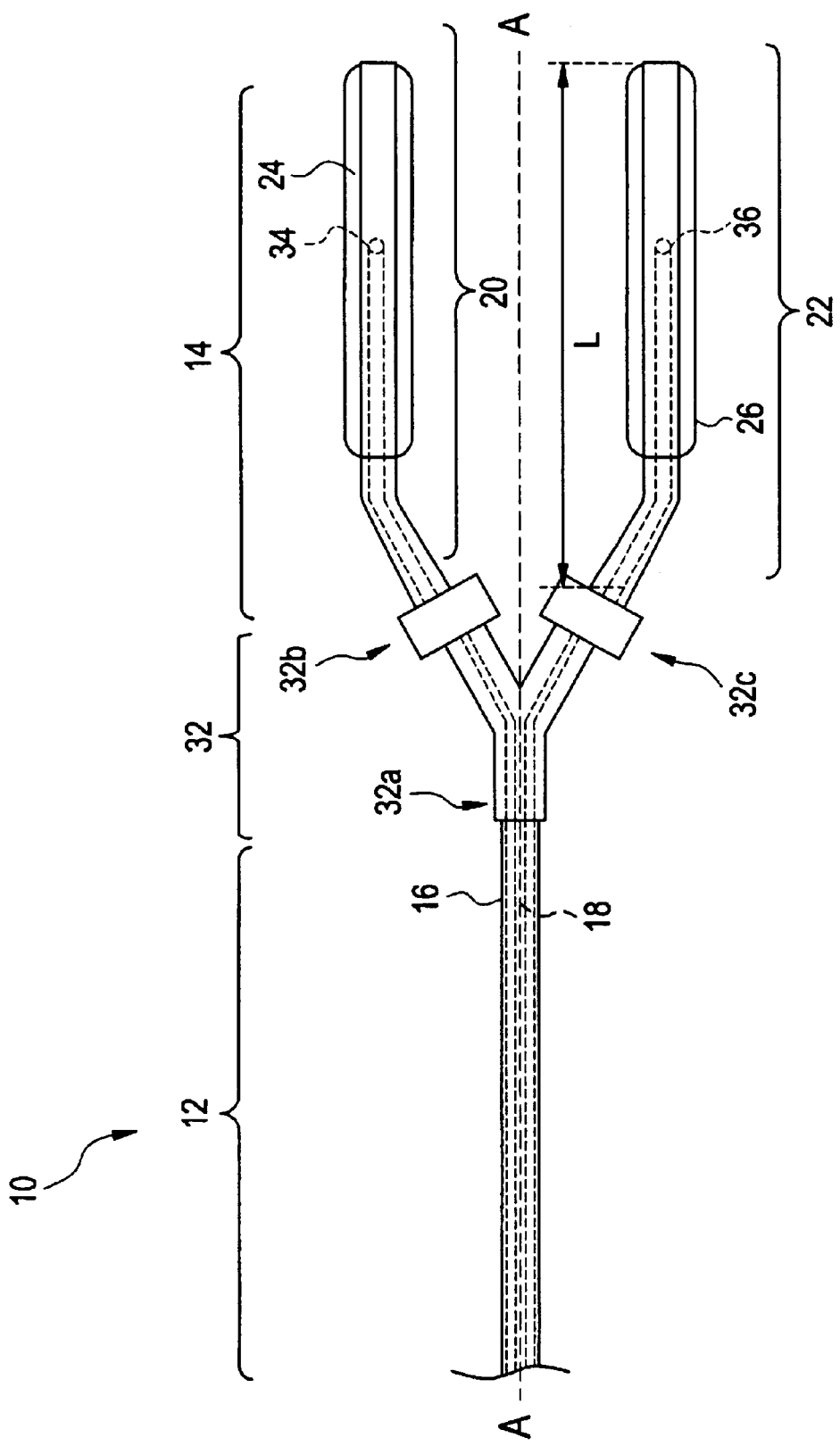
FIG. 1 is perspective view illustration of one embodiment of a brachytherapy system for proliferative tissue disorders in a patient's spinal column.

The present invention generally provides a radiotherapy system, and preferably a brachytherapy system, for delivering radiation to tissue and/or bone. While the system can be used for a variety of purposes, the system is preferably used to treat spinal metastases, and more particularly, to treat metastases on and around a patient's spinous process. FIG. 1 illustrates one embodiment of the device which generally includes a catheter member 10 having a proximal portion 12, a distal portion 14, and at least one lumen extending therethrough. As shown in FIG. 1, the catheter member 10 includes first and second lumens 16, 18 extending through the proximal and distal portions 12, 14. The distal portion 14 of the catheter 10 includes first and second branch members 20, 22 which are preferably adapted to be positioned on opposed sides of a patient's spinous process. Each branch member 20, 22 includes an anchoring element 24, 26 disposed on at least a portion thereof for anchoring the branch members 20, 22 at the treatment site. The first and second branch members 20, 22 can also be adapted to receive a radiation source through at least one of the lumens 16, 18 (or another lumen) formed in the catheter 10. The radiation source can generally be provided as a solid radiation source which can be loaded into the lumen using a conventional afterloader or as a liquid radiation source which can be loaded, for example, into anchoring elements 24, 26 using the lumen or lumens. The device is particularly advantageous in that it allows radiation to be delivered to specific regions of a patient's spine and surrounding tissue. Moreover, the treatment can be tailored depending on the intended treatment site.

The catheter member 10 can have a variety of configurations, but is preferably a semi-flexible or flexible elongate member having a proximal portion 12 and a distal portion 14 having first and second branch members 20, 22. Flexibility (or semi-flexibility) in catheter member 10 can allow the catheter member to be adapted to the curvature of a particular patient's spine. The catheter 10 further includes at least one lumen formed therein that extends through the proximal portion 12 and the first and second branch members 20, 22 of the distal portion 14. In an exemplary embodiment, a first lumen 16 extends through the proximal portion 12 and the first branch member 20, and a second, separate lumen 18 extends through the proximal portion 12 and the second branch member 22. The lumens 16, 18 can each terminate at a distal port 34, 36 formed in the first and second branch members 20, 22, respectively.

The branch members 20, 22 can be integrally formed with the proximal portion 12 of the catheter 10, or alternatively can be mated to the proximal portion 12 using a variety of mating techniques. As shown in FIG. 1, the first and second branch members 20, 22 are mated to the proximal portion 12 of the catheter 10 via a Y-shaped connector element 32. The Y-shaped connector element 32 includes a proximal end 32a that can be fixedly or removably mated to the proximal portion 12 of the catheter 10, and first and second distal ends 32b, 32c. The first distal end 32b can be fixedly or removably mated to the first branch member 20, and the second distal end 32c can be fixedly or removably mated to the second branch member 22. A variety of mating techniques can be used for mating the proximal portion 12 and the first and second branch members 20, 22 of the catheter 10 to the connector 32 including, for example, a threaded engagement, a twist lock engagement, a snap-fit engagement, and any other mechanical and/or electrical engagement mechanism. A person having ordinary skill in the art will appreciate that while a Y-shaped connector 32 is shown, a variety of connectors can be used to mate the first and second branch members 20, 22 to the proximal portion 12 of the catheter 10.

Each branch member 20, 22 can have a variety of shapes and sizes, but preferably each branch member 20, 22 has a generally elongate shape and is adapted to be positioned on opposed sides of a patient's spinous process, preferably between the spinous process and the transverse process, across one or more of the patient's vertebrae. As shown in FIG. 1, the first and second branch members 20, 22 each have a generally elongate shape and extend in a direction substantially parallel to a longitudinal axis A of the device. The branch members 20, 22 can be substantially rigid, but are preferably substantially flexible to facilitate insertion of the branch members 20, 22 between the spinous process and transverse process of one or more vertebrae in various portions of the patient's spine which may have differing curvatures. In an exemplary embodiment, the branch members 20, 22 are sufficiently flexible to allow the shape of each branch member 20, 22 to be adjusted during use of the device 10 to conform to the curvature of the portion of the patient's spine being treated. In addition, anchoring members 24, 26 are preferably sufficiently malleable (or can be placed in a sufficiently malleable state) to allow for placement of branch members 20, 22 in irregular spaces between vertebral processes or to adapt to spinal curvature.

While two branch members 20, 22 are shown, a person having ordinary skill in the art will appreciate that the catheter 10 can have a single branch member, or any number of branch members. However, for treatment of cancerous proliferation in a patient's spine by fitting branch members 20, 22 to a patient's spinal process or processes, a person of ordinary skill in the art will recognize that either two or one branches will be preferred and that, for dosing symmetry purposes, under certain circumstances two branches will be preferred.

The length L of each branch member 20, 22 can also vary depending on the intended use, but preferably each branch member 20, 22 has a length L that is sufficient to allow the branch members 20, 22 to extend along a plurality of vertebrae. In an exemplary embodiment, each branch member 20, 22 has a length L between about 4 cm and 12 cm. As previously stated, the branch members 20, 22 can be removably mated to the connector 32. Thus, the catheter 10 can be provided as a kit having several branch members with varying lengths to allow the appropriately sized branch members to be selected.

Each branch member 20, 22 further includes first and second anchoring members 24, 26 disposed thereon. The anchoring members 24, 26 can have a variety of configurations and are preferably effective to engage and anchor each branch member 20, 22 between the spinous process and the transverse process of at least one vertebral body. As shown in FIG. 1, each anchoring member 24, 26 is an expandable balloon member that is primarily sealed around the branch member 20, 22 and is in communication with one of the lumens 16, 18. The port 34 that is in communication with the first lumen 16 is disposed within the first anchoring member 24 for expanding the first anchoring element, and the port 36 that is in communication with the second lumen 18 is disposed within the second anchoring element 26 for expanding the second anchoring element.

In use, the anchoring elements 24, 26 are movable between a deflated position to allow positioning of the first and second branch members 20, 22 between the spinous process and transverse process of one or more vertebral bodies, and an inflated position, as shown, wherein air or fluid is delivered through the lumen 16, 18 and the port 34, 36 in each of the first and second branch members 20, 22 to inflate the anchoring elements 24, 26 and thereby anchor the first and second branch members 20, 22 between the spinous process and transverse process.

The anchoring elements 24, 26 can have any shape and size, but preferably each element 24, 26 has a predetermined shape in its expanded form, as shown in FIG. 1, such that, when inflated, the anchoring elements 24, 26 are adapted to securely fit between the spinous process and the transverse process to positively locate the branch members 20, 22 with respect to the target tissue to be dosed with radiation. While the size of the anchoring elements 24, 26 can be predetermined, the size can be selectable during treatment by inflating the anchoring elements 24, 26 to a desired level. In an alternative embodiment (not shown), each anchoring element 24, 26 can be an expandable cage member, and the catheter 10 can optionally include a control lever or similar mechanism for moving the expandable cage members between a contracted position and an expanded position. This configuration, as well as a number of inflatable balloon, double balloon, and other expandable surface member anchoring members as well as their operation and association with one or more lumens within device 10 is described in more detail in U.S. Pat. No. 6,413,204, issued Jul. 2, 2002, and entitled "Interstitial Brachytherapy Apparatus and Method for Treatment of Proliferative Tissue Diseases," which is incorporated herein by reference. A person having ordinary skill in the art will appreciate that a variety of anchoring elements can be used with the present invention.

Figure 2:
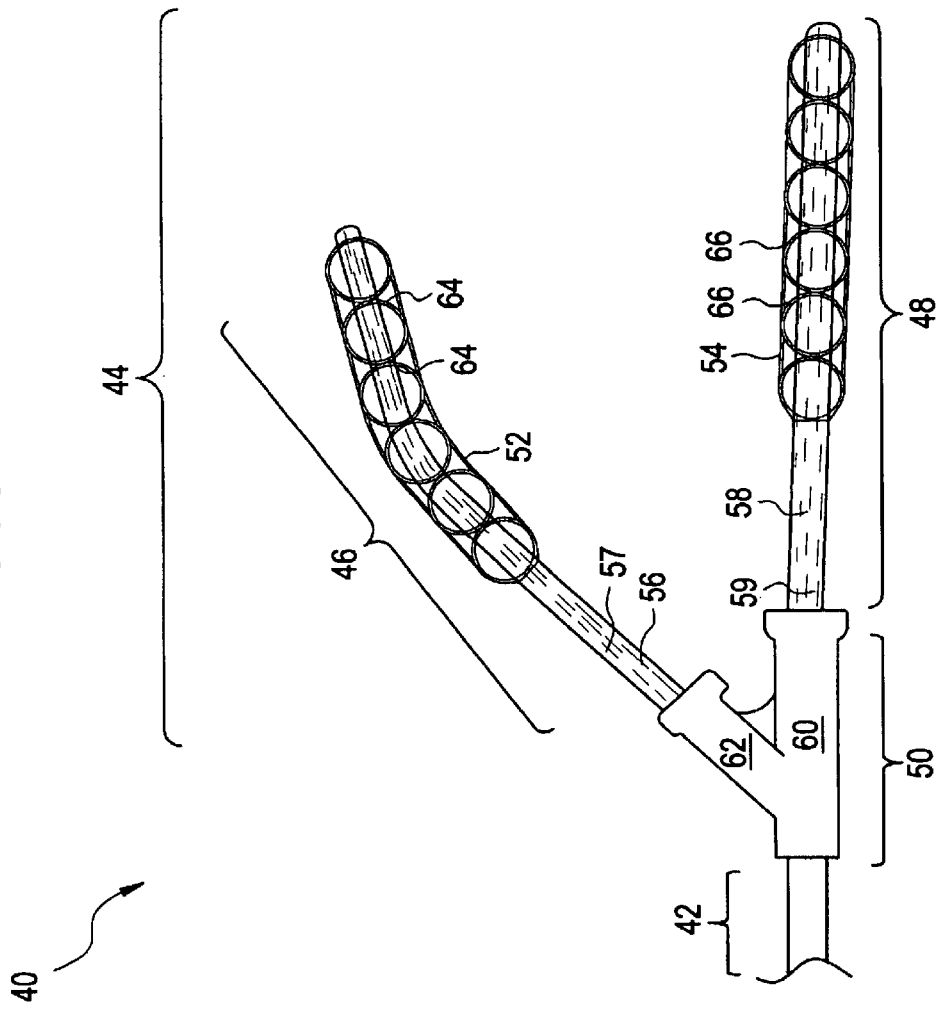
FIG. 2 is a perspective view illustration of another embodiment of a brachytherapy system for proliferative tissue disorders in a patient's spinal column.

FIG. 2 illustrates another embodiment of a catheter 40 according to the present invention. The catheter 40 is similar to catheter 10 in that it includes a proximal portion 42, a distal portion 44 having first and second branch members 46, 48, and a connector 50 disposed therebetween. The catheter 40 also includes first and second anchoring elements 52, 54 disposed on the first and second branch members 46, 48 and effective to anchor the branch members 46, 48 between a spinous process and transverse process of at least one vertebral body. First and second lumens 56, 58 extend through the catheter 40 and include distal portions (not shown) in communication with the first and second anchoring elements 52, 54 for inflating the anchoring elements 52, 54.

While the catheter 40 is very similar to catheter 10 shown in FIG. 1, the connector 50 differs in shape. As shown, the connector 50, rather than having a Y-shape, has a substantially straight portion 60 that extends between the proximal portion 42 and the second branch member 48, and a side-arm 62 that extends outward from the straight portion 60 and mates to the first branch member 46. This configuration allows the second branch member 54 to be positioned along one side of the spinous process and the first branch member 52 to extend around and along the other side of the spinous process.

Catheter member 40 further includes at least one centering mechanism 64, 66 disposed within each of the first and second anchoring elements 52, 54. The centering mechanisms 64, 66 can have a variety of configurations, and can be effective to maintain symmetry of the first and second branch members with respect to the patient's spinal column, and/or to receive a radiation source and to deliver the source uniformly to a treatment site. As shown in FIG. 2, the centering mechanisms 64, 66 are expandable balloon members that are adapted to fit within the outer anchoring element 52, 54. When inflated, the centering mechanisms 64, 66 can be spaced a predetermined distance apart from the outer anchoring element 52, 54 and/or each other, or alternatively the centering mechanism 64, 66 can engage the anchoring elements 52, 54 upon inflation. Each centering mechanism 64, 66 can also vary in shape and size, depending on the intended use. The size can, however, be selectable during treatment by inflating each centering mechanism 64, 66 to a desired level. The number of centering mechanism 64, 66 used can also vary depending on the intended use and on the length of the first and second branch members 46, 48. In an exemplary embodiment, branch members 46, 48 that have a length adapted to extend across several vertebrae include one or more centering mechanisms 64, 66 to assist in positioning each branch member between the spinous process and transverse process of each vertebra.

Figure 3:
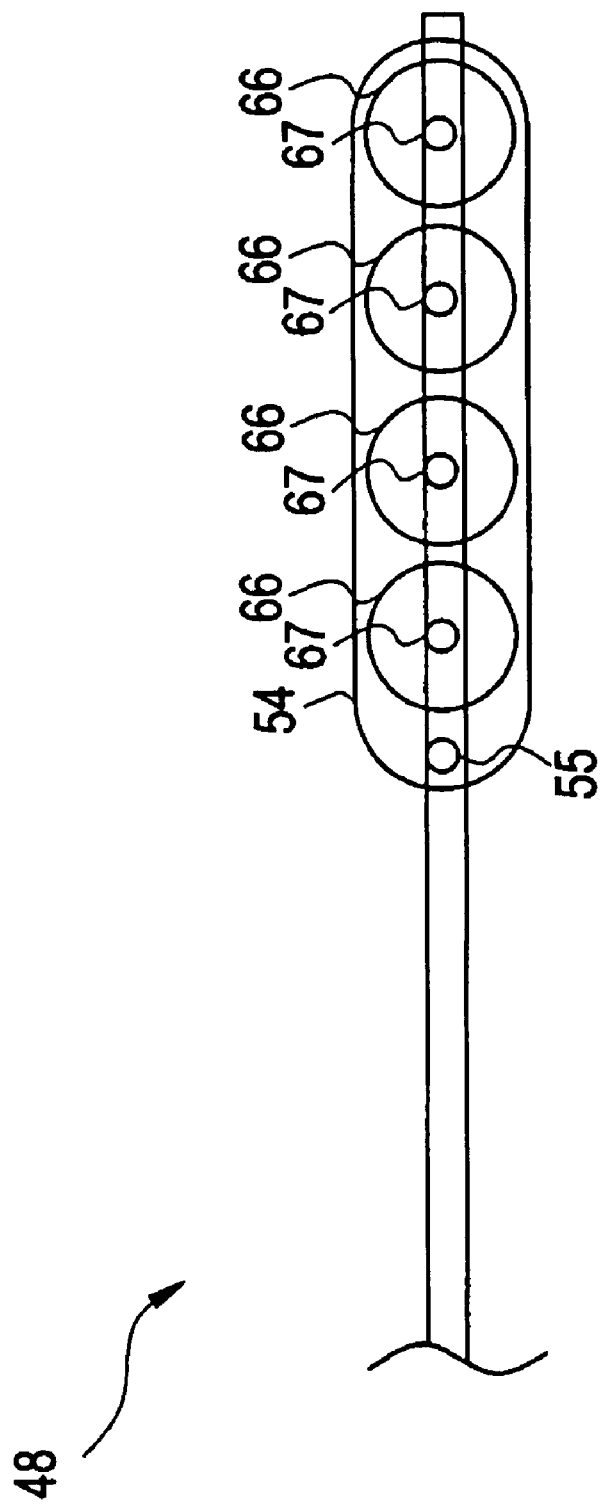
FIG. 3 is a diagram illustrating one embodiment of a branch member for use with the system of the present invention.

In use, each centering mechanism 64, 66 is in communication with a lumen in the catheter 40 for inflating the centering mechanisms 64, 66. Preferably, the catheter 40 includes four lumens 56, 57, 58, 59. The first and second lumens 56, 58 include one or more ports (not shown) that communicate with the first and second anchoring elements 52, 54, respectively. The third lumen 57 can include a port (not shown) disposed within each centering mechanism 64 in the first branch member 46, and the fourth lumen 59 can include a port (not shown) disposed within each centering mechanism 66 in the second branch member 48. By way of non-limiting example, FIG. 3 illustrates the second branch member 48 having inner lumen 58 (shown in FIG. 2) in communication with port 55 disposed within anchoring element 54. FIG. 3 further illustrates each centering mechanism 66 having a port 67 disposed therein. A person having ordinary skill in the art will appreciate that a variety of configurations can be provided for inflating the anchoring elements 52, 54 and the centering mechanisms 64, 66. In addition, centering mechanisms 64, 66 can be separately expandable or inflatable by, for example, providing separate lumens to each centering mechanism to allow for selective inflation. Where centering mechanisms 64, 66 are inflated with a radioactive treatment fluid to treat the target proliferative tissue, this configuration can allow selective treatment (by providing differing doses from the centering mechanisms) along the lengths of branch members 46 and 48 as well. Still further, centering mechanisms 64, 66 can, in one embodiment, perform the function of anchoring elements 52, 54, thus obviating the need to have separate anchoring elements.

With no limitation intended, anchoring elements and the centering mechanisms can be formed from a polymeric film wall, which may comprise a biocompatible, radiation resistant polymer. Suitable polymers include, for example, silastic rubbers, polyurethanes, polyethylene, polypropylene, polyester, and PVC. Still further, the centering mechanisms can be formed according to the balloon and/or expandable surface elements described in U.S. Pat. No. 6,413,204, issued Jul. 2, 2002, and entitled "Interstitial Brachytherapy Apparatus and Method for Treatment of Proliferative Tissue Diseases," which has been incorporated herein by reference above.

Figure 4:
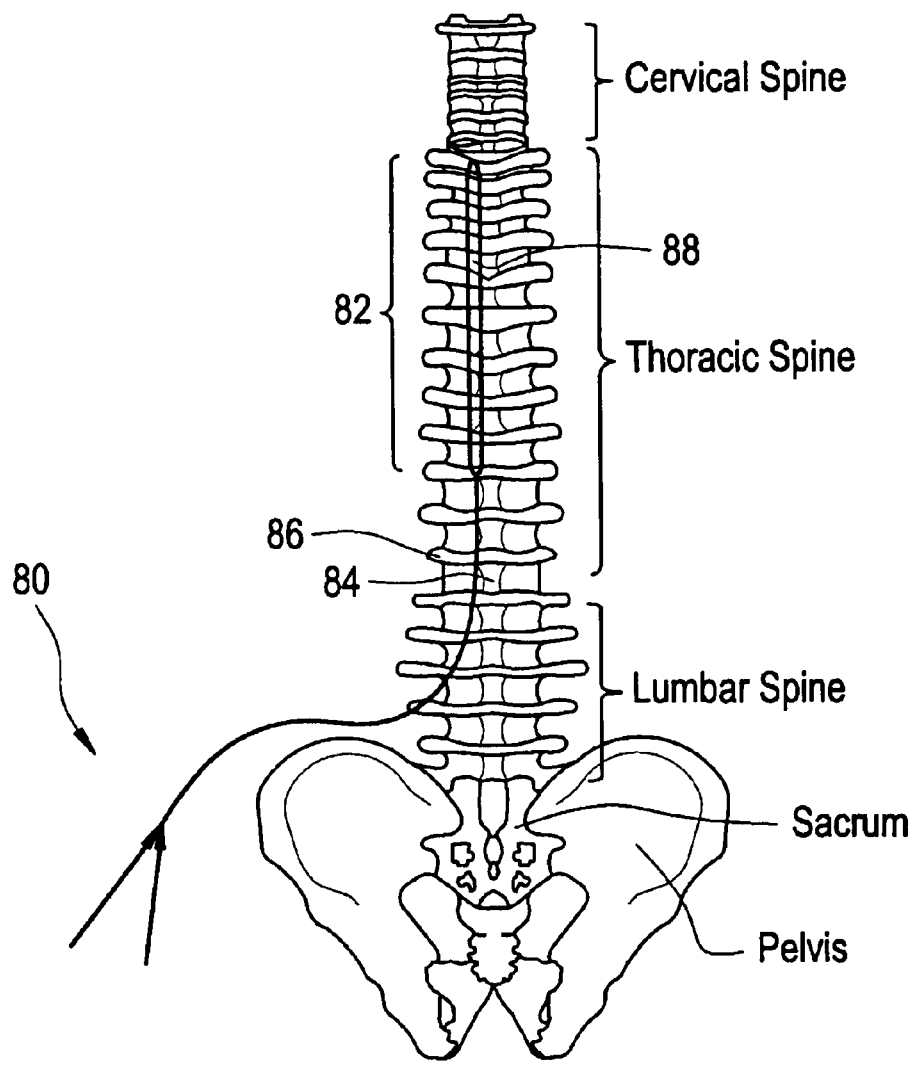
FIG. 4 is an illustration of a brachytherapy system according to the present invention positioned between a patient's spinous process and transverse process of several adjacent vertebrae.

The present invention also provides a method for treating spinal metastases. FIG. 4 illustrates one embodiment of a spinous process catheter 80 having a single branch member 82. A person having ordinary skill in the art will appreciate that a variety of catheters can be used, and that the catheter can have any number of branch members for providing radiation to various portions of a patient's spinal column. As shown, a surgeon intra-operatively places the branch member 82 of the catheter 80 into a patient's spinal column and guides it between the spinous process 84 and transverse process 86 of one or more vertebrae. Preferably, where two branch members are used, a first branch member is positioned on one side of the spinous process, and a second branch member is positioned on the second side of a patient's spinous process. The anchoring element 88 can then be inflated with air or other fluids, such as saline or a radiation absorbing fluid such as a contrast media used in angiography. Where centering mechanisms are provided, one or more of the centering mechanisms can optionally also be inflated with air or other fluids.

The catheter 80 can be pre-loaded with a radioactive source, or alternatively the radioactive source can be inserted into the catheter 80 via one of the lumens (not shown). In one embodiment, one or more solid radioactive seeds may form the radioactive source. The seed or seeds can be located within a lumen in branch member 82 by locating the seed or seeds on a wire that can be moved into, caused to dwell in, then be removed from the lumen using an afterloader such as those commonly found in hospitals in which radiotherapy is applied. The radioactive source, especially where the radioactive source is provided in the form of a liquid, can be disposed within one or more of the centering mechanism or within the anchoring element 88. Preferably, the radioactive source dwells in each centering mechanism until the prescribed dose of radiotherapy is delivered, or the radioactive source can be inserted for prescribed amounts of time on a daily or other scheduled basis until the prescribed dosage has been achieved. The radioactive source is then retrieved and the catheter 80 is removed. The application of radiotherapy using a radioactive source within catheter 80 can also be performed according to the many descriptions and examples provided in U.S. Pat. No. 6,413,204, issued Jul. 2, 2002, and entitled "Interstitial Brachytherapy Apparatus and Method for Treatment of Proliferative Tissue Diseases," which has been incorporated herein by reference above. The radiation treatment may end upon removal of the brachytherapy apparatus 80, or the brachytherapy may be supplemented by further doses of radiation supplied externally.

Suitable radiation sources for use with the system of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel. One radioactive material useful in the invention is Iotrex™, a sterile single use, non-pyrogenic solution containing sodium 3-($^{125}$I)iodo-4-hydroxybenzenesulfonate ($^{125}$I-HBS), available from Proxima Therapeutics, Inc. of Alpharetta, Ga.

Solid radioactive micro spheres of the type available from the 3M Company of St. Paul, Minn., may also be used. This radioactive source can either be preloaded into the catheter at the time of manufacture or loaded into the device after it has been implanted into the space formerly occupied by the excised tumor with one or more solid radioactive micro spheres inserted through the catheter on a wire, for example, using an afterloader (not shown). As with the liquid radioactive source embodiment, the solid radioactive source embodiment may also be used to selectively apply radiotherapy along the length of catheter 80. A plurality of seeds can be provided in a spaced relation along a wire so that they are located proximate to the region of selective treatment. Alternatively, one or more seeds can be moved by the afterloader so as to provided desired dwell times proximate to regions of selective treatment.

The system of the present invention can also have a variety of other configurations. For example, the device can be adapted to control the distribution of radiation to tissue surrounding the treatment site. One advantage to controlling the distribution of radiation to tissue surrounding the treatment site is that a minimum prescribed dose can be delivered to the tissue in the target treatment region without overexposing radiation-sensitive tissue, which can cause healthy tissue necrosis. By way of non-limiting example, referring to FIG. 2, each centering mechanism 64, 66 can be effective to receive a radiation source and to position the radiation source a predetermined distance apart from each anchoring element 52, 54, thereby providing a minimum absorbed dose for delivering radiation to tissue adjacent the anchoring element. This configuration is described in more detail in U.S. Pat. No. 6,413,204, issued Jul. 2, 2002, and entitled "Interstitial Brachytherapy Apparatus and Method for Treatment of Proliferative Tissue Diseases," which has been incorporated herein by reference above. In general, the centering mechanisms and the anchoring elements have a volume that is configured to provide an absorbed dose within a predetermined range throughout a target tissue.

In another embodiment, at least one of the anchoring element 52, 54 and/or the centering mechanisms 64, 66 can be partially coated with a radio-opaque material effective to shield radiation sensitive tissue from a portion of the radiation source. The coating (not shown) can be strategically positioned to shield radiation sensitive tissue, and/or to provide an asymmetric isodose curve as described in U.S. Pat. No. 6,482,142, issued on Nov. 19, 2002, and entitled "Asymmetric Radiation Dosing Apparatus and Method," which is incorporated herein by reference.

Radio-opaque materials suitable for coating onto an expandable surface include, for example, barium, tungsten, bismuth, tantalum, and tin. As an alternative to coating the anchoring elements and/or the centering mechanisms with a radio-opaque material, a radiation-blocking or absorbing shield (not shown) can be positioned between each anchoring element and the centering mechanisms disposed therein, or within the centering mechanisms to produce a desired isodose curve. A person having ordinary skill in the art will appreciate that other configurations may be employed to achieve the desired isodose curves and/or shielding of radiation sensitive tissue. In particular with the present invention, longitudinal shielding could be provided between the radiation source and the patient's spinal cord in order to treat cancerous tissue in and around the spine while protecting the spinal cord from radiation.

In yet another embodiment, the radiation source itself can be configured to provide radiation to a desired region of tissue surrounding the interstitial space. By way of non-limiting example, the radiation source can comprise a wire having one or more solid radioactive particles located thereon. The radioactive source can either be preloaded into the catheter at the time of manufacture, or loaded into the device after it has been implanted into the space formerly occupied by the excised tumor. If loaded after implantation, the solid radiation emitting material can be inserted through one of the lumens 56, 57, 58, 59 (or through another lumen) on a wire, for example, using an afterloader (not shown). In this embodiment, the catheter 40 may need to be adapted to have a size sufficient to receive such a radiation source. The radiation source has an asymmetric configuration with respect to a longitudinal axis of the instrument. That is, radiation source is shaped so as to result in an isodose profile that varies radially about the longitudinal axis A. The asymmetrically shaped isodose curve may be created by providing a plurality of solid radioactive particles on a curved wire in a spaced apart relationship. This configuration will result in certain of the solid radioactive particles being farther from the longitudinal axis of the instrument than others, and will result in the illustrated asymmetric isodose profile.

One way to provide the radioactive source configuration is to form wire from a solid or tubular shape memory alloy such as nickel-titanium alloys known in the art to have such properties. Wire can then be preformed to the desired shape, can be compressed into a substantially straight configuration to pass through the first lumen, and will resume its desired shape once inside volume where wire will be free from steric constraints imposed inside the first lumen. The resulting asymmetric isodose curve can be further tailored by using solid radioactive particles having differing specific activities to achieve the desired dosing. Such a configuration is described in more detail in U.S. Pat. No. 6,482,142, issued on Nov. 19, 2002, and entitled "Asymmetric Radiation Dosing Apparatus and Method."

A person having ordinary skill in the art will appreciate that the foregoing is only illustrative of the principles of the invention, and that various modifications can be made by those skilled in the art without departing from the scope and spirit of the invention. All references cited herein are expressly incorporated by reference in their entirety.

What is claimed is:

1. A brachytherapy device, comprising:
a catheter member having a proximal portion, a distal portion, and at least one lumen extending therethrough, the distal portion of the catheter member including first and second branch members adapted to be positioned on opposed sides of at least one of a patient's spinous processes; and
first and second elongate anchoring elements disposed on the first and second branch members;
wherein the brachytherapy device is adapted to receive a radiation source through the at least one lumen into the first and second branch members for delivering radiation to tissue surrounding the at least one spinous process.

2. The device of claim 1, further comprising at least one centering mechanism disposed on each of the first and second branch members, each centering mechanism being effective to maintain symmetry of the first and second branch members with respect to a patient's spinal column.

3. The device of claim 2, wherein the first and second anchoring elements comprise first and second outer expandable balloons, and wherein each centering mechanism comprises an inner expandable balloon.

4. The device of claim 3, wherein the device includes a plurality of inner expandable balloons on each branch, each inner expandable balloon having a size adapted to receive a predetermined amount of a fluid radiation source such that varying doses of radiation can be delivered along a length of the outer expandable balloon.

5. The device of claim 2, wherein the first and second anchoring elements are adapted to be positioned between a spinous process and transverse process of at least one vertebral body, and to extend along a length of a patient's spinal column, such that the first and second anchoring elements, when expanded, engage and anchor the first and second branch members between the spinous process and transverse process of at least one vertebral body.

6. The device of claim 3, further comprising a radiation source in the form of a liquid and wherein each inner expandable balloon is effective to removably receive the radiation source.

7. The device of claim 3, wherein each inner expandable balloon is effective to position a radiation source at a predetermined distance apart from the first and second outer expandable balloon to provide a minimum absorbed dose for delivering radiation to tissue adjacent to the outer expandable balloons.

8. The device of claim 1, further comprising a radiation source in the form of at least one solid radiation source disposed on at least one elongate member.

9. The device of claim 8, wherein a plurality of solid radiation sources are disposed in a spaced apart relationship on a single elongate member.

10. The device of claim 1, wherein the catheter member is flexible.

11. The device of claim 1, wherein the device is adapted to provide varying doses of radiation along a length of each of the first and second elongate anchoring elements.

12. The device of claim 1, wherein the first and second elongate anchoring elements each have a length adapted to span a plurality of vertebrae.

13. The device of claim 12, wherein the length is between about 4 cm and 12 cm.

14. A brachytherapy device, comprising:
an elongate catheter member having a proximal portion, a distal portion, an inflation lumen, and at least one source lumen; and
a plurality of inner centering mechanisms disposed around the catheter member, each of the plurality of inner centering mechanisms being in fluid communication with said at least one source lumen;
wherein the device is adapted to receive a radiation source to deliver radiation to tissue surrounding the device.

15. The device of claim 14, further comprising an outer anchoring member disposed around the distal portion of the catheter member and in communication with the inflation lumen, the outer anchoring member being adapted to anchor the catheter member between a spinous process and transverse process of at least one vertebral body, and to extend along a length of a patient's spinal column.

16. The device of claim 15, wherein the device is adapted to provide varying doses of radiation along a length of the outer anchoring member.

17. The device of claim 15, wherein the outer anchoring member has a length adapted to span a plurality of vertebrae.

18. The device of claim 17, wherein the length is between about 4 cm and 12 cm.

19. The device of claim 15, wherein the plurality of centering mechanisms are disposed within the outer anchoring member and are effective to maintain symmetry along a length of the distal portion of the elongate catheter member.

20. The device of claim 19, wherein each of the plurality of centering mechanisms is effective to position a radiation source at a predetermined distance apart from the outer anchoring member to provide a minimum absorbed dose for delivering radiation to tissue adjacent to the outer anchoring member.

21. The device of claim 20, further comprising a radiation source in the form of at least one solid radiation source disposed on at least one elongate member.

22. The device of claim 21, wherein a plurality of solid radiation sources are disposed in a spaced apart relationship on a single elongate member.

23. The device of claim 19, wherein the outer anchoring member comprises an outer expandable balloon, and wherein each of the plurality of centering mechanisms comprises an inner expandable balloon.

24. The device of claim 23, wherein the plurality of inner expandable balloons each have a size adapted to receive a predetermined amount of a fluid radiation source such that varying doses of radiation can be delivered along a length of the outer expandable balloon.

25. The device of claim 14, further comprising a radiation source in a fluid form, wherein each of the plurality of centering mechanisms is effective to removably receive the radiation source.

26. The device of claim 14, wherein the elongate catheter member is flexible.

27. A method for treating spinal metastases, comprising:
providing at least one brachytherapy apparatus for delivering radioactive emissions, the apparatus having
a catheter member having proximal and distal ends and at least one lumen extending therethrough,
at least one anchoring element disposed proximate to the distal end of the catheter, and
a radiation source disposable through the at least one lumen in the catheter for delivering radiation to the tissue surrounding the anchoring element;
intraoperatively placing at least one brachytherapy apparatus between a spinous process and transverse process of at least one vertebral body along a length of the patient's spinal column;
providing a controlled dose of radiation to tissue surrounding the apparatus; and
removing the brachytherapy apparatus.

28. The method of claim 27, wherein a radiation source is placed into the brachytherapy apparatus after placement of the apparatus between the spinous process and transverse process of at least one vertebral body.

29. The method of claim 28, wherein the radiation source is removed from the apparatus before removal of the apparatus.

30. The method of claim 27, wherein the apparatus further includes at least one centering mechanism disposed around the catheter member and within the anchoring element, the at least one centering mechanism being effective to provide symmetry to the anchoring element with respect to a patient's spinal column.

31. The method of claim 30, wherein the anchoring element comprises an outer expandable balloon, and wherein each of the at least one centering mechanisms comprises an inner expandable balloon.

32. The method of claim 31, wherein the apparatus includes a plurality of inner expandable balloons, each inner expandable balloon having a size adapted to receive a predetermined amount of a fluid radiation source such that varying doses of radiation can be delivered along a length of the outer expandable balloon.

33. The method of claim 27, wherein the distal end of the catheter member of the apparatus includes first and second branch members, each branch member having an anchoring element disposed therein for anchoring the branch member between a spinous process and transverse process of at least one vertebral body along a length of a patient's spinal column.

34. The method of claim 33, wherein the apparatus further includes a least one centering mechanism disposed around each of the first and second branch members and within each anchoring element, each centering mechanism being effective to provide symmetry to each anchoring element with respect to a patient's spinal column.

35. The method of claim 34, wherein each anchoring element comprises an outer expandable balloon, and wherein each centering mechanism comprises an inner expandable balloon.

36. The method of claim 35, wherein the apparatus includes a plurality of inner expandable balloons, each inner expandable balloon having a size adapted to receive a predetermined amount of a fluid radiation source such that varying doses of radiation can be delivered along a length of each outer expandable balloon.

37. The method of claim 35, wherein each inner expandable balloon is effective to removably receive the radiation source, and wherein the radiation source is in a fluid form.

38. The method of claim 27, wherein the radiation source comprises at least one solid radiation source disposed on at least one elongate member.

39. The method of claim 38, wherein a plurality of solid radiation sources are disposed in a spaced apart relationship on a single elongate member.

40. The method of claim 27, wherein the catheter member is flexible.

41. The method of claim 27, wherein the apparatus is adapted to provide varying doses of radiation along a length of the elongate anchoring element.

42. The method of claim 27, wherein the elongate anchoring element has a length adapted to span a plurality of vertebrae.

43. The method of claim 42, wherein the length is between about 4 cm and 12 cm.

* * * * *